US00PP37411P3

(12) United States Plant Patent
Mussche

(10) Patent No.: US PP37,411 P3
(45) Date of Patent: May 5, 2026

(54) ***HOYA* PLANT NAMED 'G4Y0002'**

(50) Latin Name: *Hoya carnosa*
Varietal Denomination: G4Y0002

(71) Applicant: Grow 4 You B.V.

(72) Inventor: Erik Mussche, Bogor (ID)

(73) Assignee: Grow 4 You B.V., Enter (NL)

( * ) Notice: Subject to any disclaimer, the term of this patent is extended or adjusted under 35 U.S.C. 154(b) by 0 days.

(21) Appl. No.: 18/831,491

(22) Filed: Feb. 26, 2025

(65) Prior Publication Data

US 2025/0280747 P1 Sep. 4, 2025

(30) Foreign Application Priority Data

Mar. 1, 2024 (QZ) ..... PBR 20240575

(51) Int. Cl.
*A01H 6/08* (2018.01)
*A01H 5/00* (2018.01)
*A01H 5/12* (2018.01)

(52) U.S. Cl.
USPC ..... Plt./380
CPC ..... *A01H 6/08* (2018.05); *A01H 5/12* (2013.01)

(58) Field of Classification Search
USPC ..... Plt./373, 380
See application file for complete search history.

(56) References Cited

U.S. PATENT DOCUMENTS

PP3,105 P * 4/1972 Cobia ..... Plt./380

* cited by examiner

*Primary Examiner* — Karen M Redden
(74) *Attorney, Agent, or Firm* — Samuel R. McCoy, Jr.

(57) ABSTRACT

A new and distinct *Hoya carnosa* plant named 'G4Y0002' which is characterized by uniquely variegated foliage borne on scandent stems, brown juvenile stems, juvenile foliage that is centered brown and broadly margined with a vibrant pink general coloration, mature foliage that is green and broadly margined with a pale-yellow general coloration, and the stability of these characteristics from generation to generation.

3 Drawing Sheets

Latin name of the genus and species: The Latin name of the genus and species of the novel variety disclosed herein is *Hoya carnosa.*

Variety denomination: The inventive variety of *Hoya* disclosed herein has been given the variety denomination 'G4Y0002'.

CROSS REFERENCE TO RELATED APPLICATIONS

This application claims priority to the Community Plant Variety Rights application number 2024/0575, filed Mar. 1, 2024, which is herein incorporated by reference.

BACKGROUND OF THE INVENTION

Parentage: The new plant originated as a spontaneous, partial-plant, branch mutation. The mutation was discovered at a greenhouse in Bogor, Indonesia in January of 2022, growing amongst a plurality of cultivated *Hoya carnosa* 'Tri-Color' plants (U.S. Plant Pat. No. 2,950). The mutation exhibited conspicuously variegated foliage and a high degree of vibrant pink coloration of the juvenile foliage, relative to the parent. The mutation was isolated and grown to a mature size in order to evaluate stability and uniqueness of the characteristics first observed. Upon confirmation of the stability and uniqueness, the new plant was selected for commercialization and given the name, 'G4Y0002'.

Asexual Reproduction: Asexual reproduction of the new cultivar 'G4Y0002', by way of softwood stem cuttings, was first initiated in May of 2022 in a commercial production greenhouse in Bogor, Indonesia. After three subsequent generations have shown that the unique features of the instant cultivar are stable and reproduced true to type.

SUMMARY OF THE INVENTION

The cultivar 'G4Y0002' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'G4Y0002'. These characteristics in combination distinguish 'G4Y0002' as a new and distinct *Hoya* cultivar:

1. *Hoya* 'G4Y0002' exhibits a vining habit with an abundance of variegated ovate to elliptic foliage in a whorled arrangement that grows opposite decussate vertically along the entire length of the scandent stems; and
2. *Hoya* 'G4Y0002' exhibits brown juvenile stems; and
3. *Hoya* 'G4Y0002' exhibits juvenile foliage that is centered brown and broadly margined with red to greyed-purple, generally appearing as a vibrant pink color; and
4. *Hoya* 'G4Y0002' exhibits mature foliage that is green and broadly margined with light greyed-yellow, generally appearing as a pale-yellow coloration.

BOTANICAL DESCRIPTION OF THE PLANT

Figure 1:
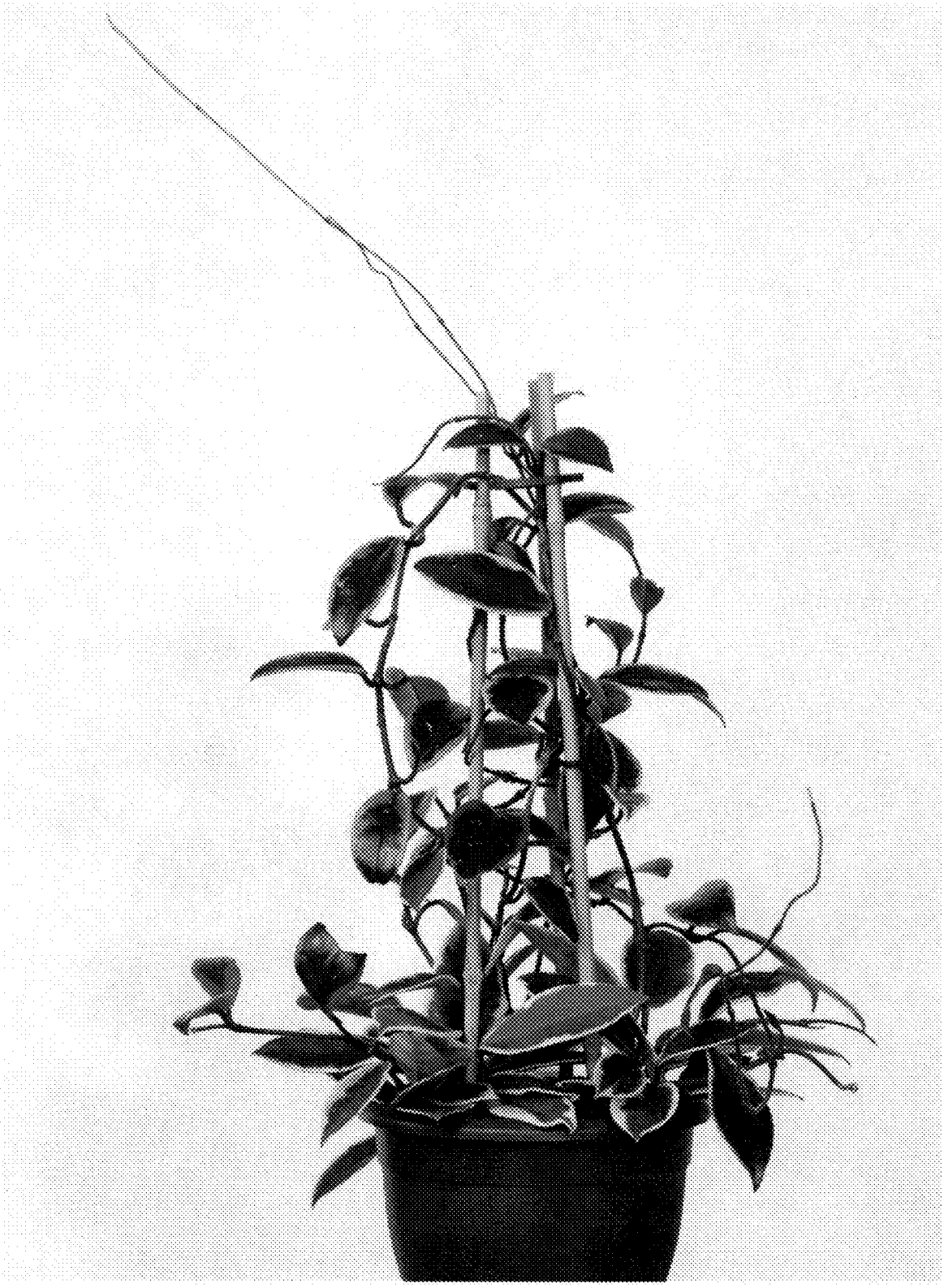
FIG. 1 illustrates, as nearly true as it is reasonably possible to make the same in color photographs of this type, an exemplary 20-week-old 'G4Y0002' plant in an 18 cm nursery pot in a greenhouse in Honselersdijk, the Netherlands.
Figure 2:
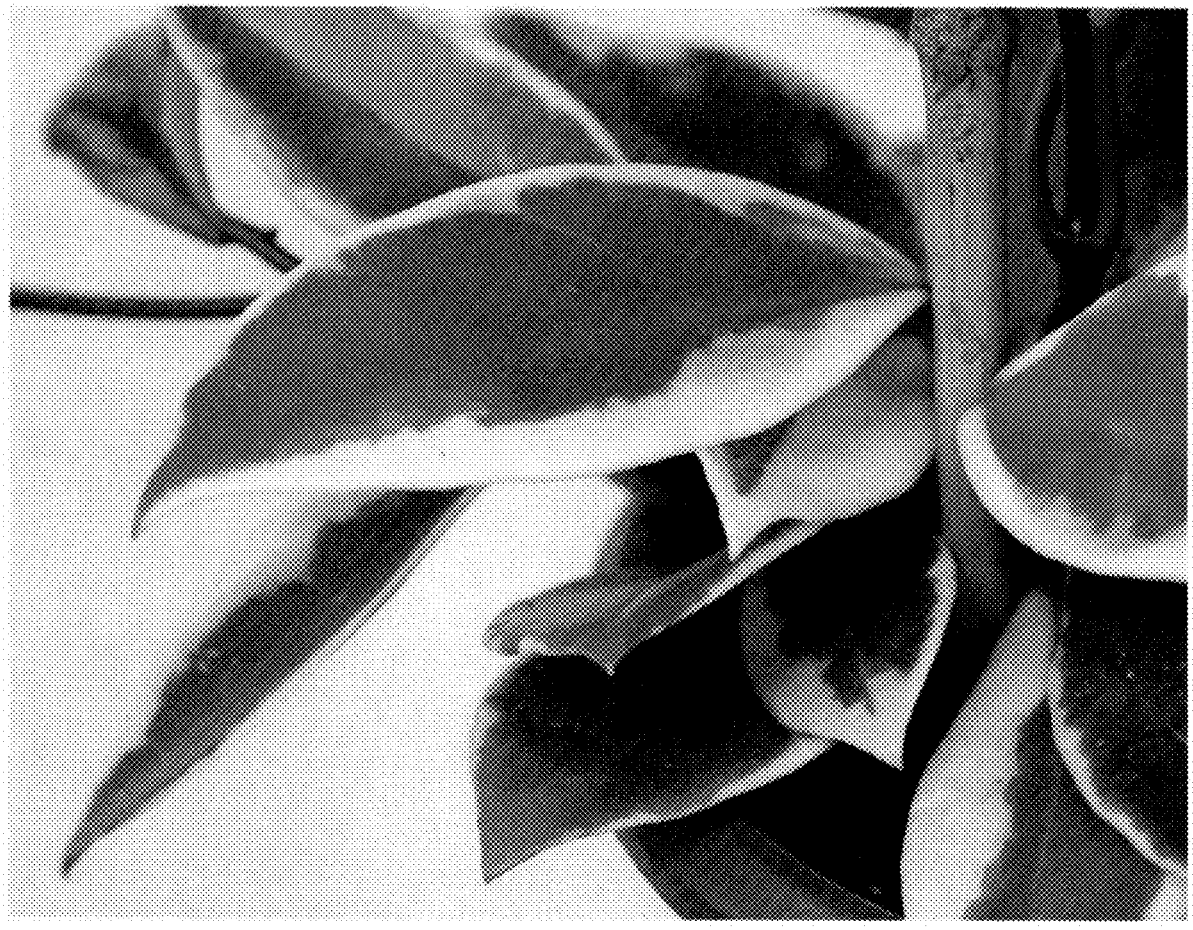
FIG. 2 illustrates, as nearly true as it is reasonably possible to make the same in color photographs of this type, the mature foliage of 'G4Y0002'.
Figure 3:
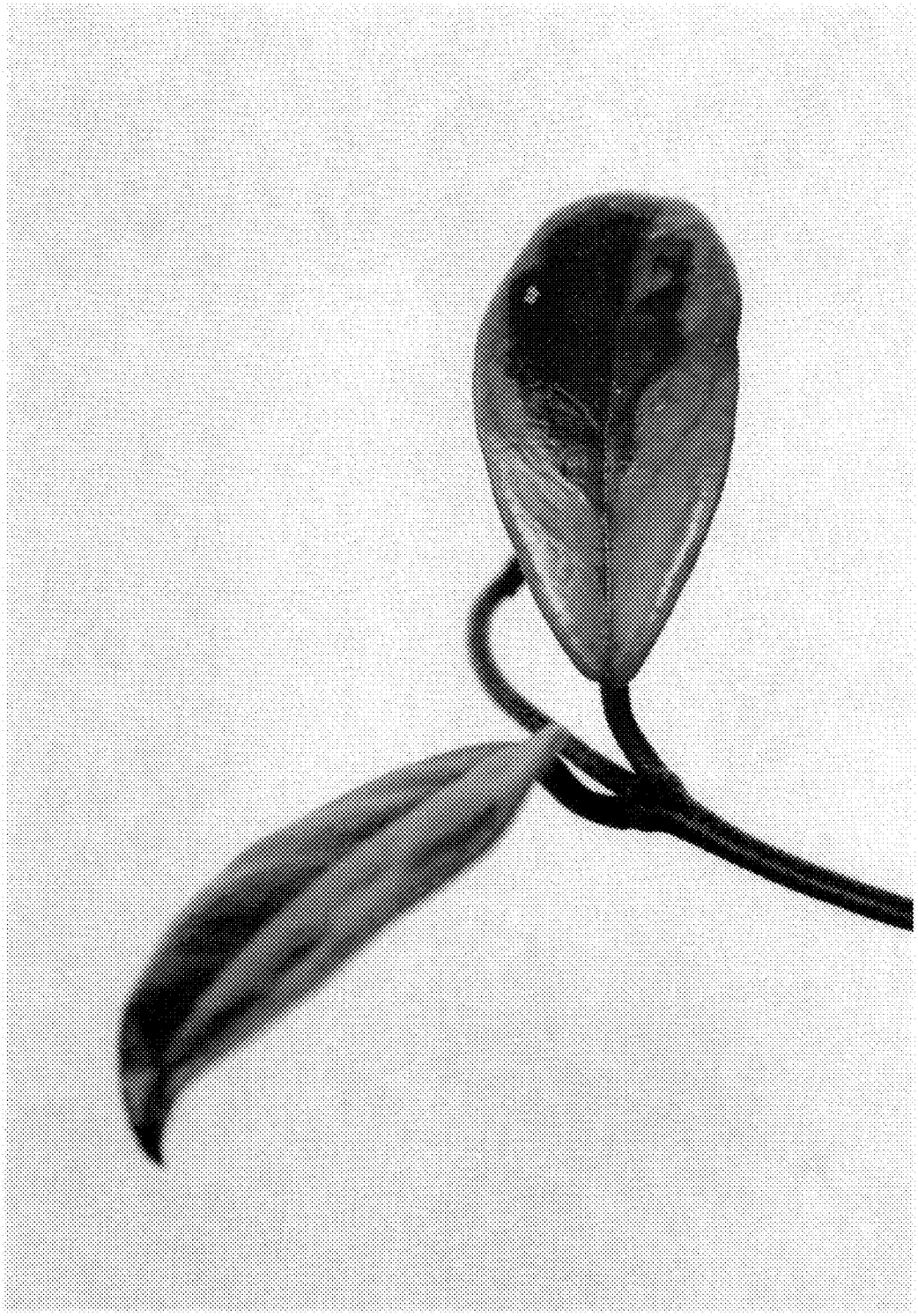
FIG. 3 illustrates, as nearly true as it is reasonably possible to make the same in color photographs of this type, the juvenile foliage of 'G4Y0002'.

The following observations and measurements were made in February of 2024 and describe a 12-month-old 'G4Y0002' plant grown in a 17 cm nursery pot with 21 cm bamboo stakes grown in a climate-controlled greenhouse in Honselersdijk, the Netherlands. Plants were irrigated regularly and given supplemental lighting to provide a consistent 14 hours of light per day. No fertilizer applications or chemical pest control measures were utilized during production.

Those skilled in the art will appreciate that certain characteristics will vary with older or, conversely, with younger plants. 'G4Y0002' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, sixth edition.

A botanical description of 'G4Y0002' and comparisons with the parent and most similar commercial variety of *Hoya* are provided below.

Plant description:

*Growth habit.*—Evergreen vining perennial.

*Average height.*—Vining plant with indeterminate growth; approximately 78.1 cm as observed.

*Average width.*—Vining plant with indeterminate growth; approximately 17.7 cm as observed.

*Propagation method.*—Softwood stem cuttings; rooting is initiated in approximately 20 weeks, and approximately 2 to 4 weeks are required to produce a rooted cutting when grown in a greenhouse with at least 90% humidity and an ambient average temperature of 22 degrees Celsius.

*Time to produce a finished plant.*—Approximately 5 months are required to produce a fully rooted and marketable plant in a 17 cm nursery container, when grown under greenhouse conditions.

*Disease and pest resistance or susceptibility.*—Plants have not been observed to be susceptible or resistant to pathogens and pests common to *Hoya elliptica*.

*Environmental tolerances.*—Adapt to at least USDA Zones 10 through 12; moderate to high tolerance to rain; moderate tolerance to wind; low tolerance to drought.

Root system:

*General.*—Exhibits a relatively shallow root system with adventitious roots arising along the stems.

*Branching.*—Freely branched.

*Density.*—Moderately dense.

*Distribution.*—Relatively shallow.

*Texture.*—Fleshy; smooth; lacking root hairs.

*Color.*—Nearest to a combination of white and greyed-yellow, nearest to RHS NN155D and 162C.

Stem:

*Branching habit.*—Basally clumping scandent stems, vertically climbing and twining around stakes or in trellises.

*Number of main stems per plant.*—3.

*Number of lateral branches per plant.*—None.

*Aspect.*—Terete.

*Length of main stems.*—25.6 cm.

*Diameter of main stems.*—0.225 cm at the base.

*Internode length on main stems.*—5.0 cm average.

*Attitude.*—Vining; scandent.

*Strength.*—Strong, highly flexible.

*Texture and luster.*—Strigose, moderately to densely covered with short hairs, and glossy. Hairs are on average 0.5 mm in length and colored greyed-brown, difficult to distinguish from surrounding, nearest to RHS 199D.

*Color, juvenile.*—Brown, nearest to RHS 200A.

*Color, mature.*—Green, a blend of RHS 197A and 197B.

*Color at internodes.*—Greyed-green, nearest to a combination of RHS 197A and 197B.

Foliage:

*Arrangement.*—Whorled at the base of the stem, as the vining plant climbs leaves become opposite decussate.

*Division.*—Simple.

*Attachment.*—Petiolate.

*Abundance.*—Approximately 10 leaves per lateral branch at the time of observation.

*Lamina.*—Dimensions — On average, 7.9 cm long and 3.8 cm wide; average thickness is 1.75 mm. Shape — Ovate to elliptic. Aspect — Near-flat. Apex — Aristate to apiculate. Base — Acute to shallow truncate. Margin — Entire; not undulated. Texture and luster — Glabrous, coriaceous, and smooth. Color — Juvenile foliage, adaxial surface — Brown, nearest to RHS 200A; broadly and irregularly margined with a blend of red and greyed-purple, nearest to RHS 53D and 184D; sparsely to moderately covered with small, irregularly shaped blotches that are colored greyed-green, nearest 198D. Juvenile foliage, abaxial surface — Greyed-green, nearest to RHS 197B, and lightly suffused yellow-green, nearest to RHS 148B; broadly and irregularly margined with greyed-red, nearest to RHS 182D; narrowly edged with greyed-purple along the margins of the lamina, nearest to RHS 185A. Mature foliage, adaxial surface — A blend of green and yellow-green, nearest to RHS NN137A and 147A; broadly and irregularly margined with greyed-yellow, nearest to a combination of RHS 160C and 160D; sparsely covered with small, irregularly shaped blotches that are colored greyed-green, nearest 198D. Mature foliage, abaxial surface — Yellow-green, nearest to a blend of RHS 146C and 148B; broadly and irregularly margined greyed yellow, nearest to a combination of RHS 160C and 160D. Venation — Pattern — Parallel venation with brochidodromous secondary lateral veins. Venation color, adaxial surface — Green to yellow-green, nearest a blend of RHS NN137A and 147A. Venation color, abaxial surface — Yellow-green, nearest to RHS 146C and slightly tinted greyed — red proximally, nearest to RHS 182B.

*Petiole.*—Length — 2.0 cm. Width — 0.3 cm. Aspect — Terete. Texture — Juvenile leaves moderately strigose, covered with short adpressed hairs averaging in length at 0.5 mm; colored greyed-brown, nearest to RHS 199D. Once leaves reach maturation, petioles are smooth and glabrous. Luster — Slightly glossy. Strength — Moderately to highly strong. Color, juvenile foliage — Greyed-purple to brown, nearest to a combination of RHS 185C, 185D and N200A. Color, mature foliage — Greyed-purple to brown, nearest to a combination of RHS 185C.

Inflorescence: No Inflorescence observed to date.

Seed and fruit: No seeds or fruit observed to date.

COMPARISONS WITH THE PARENT PLANT

Plants of the new cultivar 'G4Y0002' differ from the parent, *Hoya carnosa* 'Tri-Color' by the characteristics described in Table 1.

TABLE 1

| Characteristic | 'G4Y0002' | 'Tri-Color' |
|---|---|---|
| General coloration of the adaxial surface of the juvenile foliage. | Brown and broadly margined with red to greyed-purple, generally appearing as a vibrant pink color. | The typical juvenile foliage is dark green and more narrowly margined with light pink; occasionally, a juvenile leaf will emerge nearly homogenously pale yellow with pink suffusion or pale yellow with a central irregular blotch. |
| General coloration of the adaxial surface of the mature foliage. | Green and broadly margined with light greyed-yellow, generally appearing as a pale-yellow coloration. | Irregularly centered with pale green-yellow with light yellow-green blotches, and margined dark green. |
| General coloration of the juvenile stems. | Brown. | Greyed-red to greyed-purple. |

COMPARISON WITH THE MOST SIMILAR *HOYA* CULTIVAR KNOWN TO THE INVENTOR

Plants of the new cultivar 'G4Y0002' differ from *Hoya carnosa* 'Rubra' (U.S. Plant Pat. No. 3,105) in the following characteristics described in Table 2 below.

TABLE 2

| Characteristic | 'G4Y0002' | 'Rubra' |
|---|---|---|
| General coloration of the adaxial surface of the juvenile foliage. | Variegated; brown and broadly margined with red to greyed-purple, generally appearing as a vibrant pink color. | Irregularly centered with pale green-yellow to greyed-yellow; central portion irregularly bordered with light yellow-green blotches; margined mid-green; central portions of the laminar are lightly to moderately suffused with pink. |
| General coloration of the adaxial surface of the mature foliage. | Green and broadly margined with light greyed-yellow, generally appearing as a pale-yellow coloration. | Irregularly centered with pale greyed-yellow; central portion irregularly bordered with light yellow-green blotches; margined mid-green, |
| General coloration of the juvenile stems. | Brown. | Greyed-red. |

That which is claimed is:

1. A new and distinct *Hoya carnosa* plant named 'G4Y0002', substantially as described and illustrated herein.

* * * * *